United States Patent [19]
Leunissen et al.

[11] Patent Number: 5,872,013
[45] Date of Patent: *Feb. 16, 1999

[54] UNIVERSALLY APPLICABLE DETECTION SYSTEM BASED ON ULTRA SMALL COLLOIDAL METAL PARTICLES

[75] Inventors: Johannes Leonardus Maria Leunissen, Merksplas; Marc Joris De Brabander, Zoersel, both of Belgium; Petrus Franciscus Elisabeth Maria Van de Plas, Breda, Netherlands

[73] Assignee: Janssen Pharmaceutica N.V., Beerse, Belgium

[ * ] Notice: This patent issued on a continued prosecution application filed under 37 CFR 1.53(d), and is subject to the twenty year patent term provisions of 35 U.S.C. 154(a)(2).

[21] Appl. No.: 539,131

[22] Filed: Oct. 4, 1995

Related U.S. Application Data

[63] Continuation of Ser. No. 160,449, Dec. 1, 1993, abandoned, which is a continuation of Ser. No. 034,640, Mar. 22, 1993, abandoned, which is a continuation of Ser. No. 920,028, Jul. 27, 1992, abandoned, which is a continuation of Ser. No. 271,798, Nov. 15, 1988, abandoned.

[30] Foreign Application Priority Data

Nov. 16, 1987 [EP] European Pat. Off. ............. 87202231

[51] Int. Cl.[6] .................................................. G01N 33/553
[52] U.S. Cl. ...................... 436/525; 435/7.92; 435/7.93; 435/7.94; 435/7.95; 436/501; 436/512; 436/518; 436/801; 530/391.1; 530/391.3; 530/811; 252/302
[58] Field of Search ................................. 435/7.92, 7.93, 435/7.94, 7.95, 960; 436/501, 512, 518, 525, 801; 530/391.1, 391.3, 811; 252/302

[56] References Cited

U.S. PATENT DOCUMENTS

| | | |
|---|---|---|
| 4,206,094 | 6/1980 | Yen et al. . |
| 4,313,734 | 2/1982 | Leuvering . |
| 4,420,558 | 12/1983 | De Mey et al. . |
| 4,446,238 | 5/1984 | De Mey et al. ........................ 436/527 |
| 4,752,567 | 6/1988 | DeBrabander et al. ............ 436/525 X |
| 4,775,636 | 10/1988 | Moeremans et al. ................... 436/518 |
| 4,877,647 | 10/1989 | Klabunde ................................ 427/123 |
| 5,120,643 | 6/1992 | Ching et al. .......................... 435/7.92 |

FOREIGN PATENT DOCUMENTS

| | | |
|---|---|---|
| 158 746 | 10/1985 | European Pat. Off. . |
| 165 643 | 12/1985 | European Pat. Off. . |
| 167 834 | 1/1986 | European Pat. Off. . |

OTHER PUBLICATIONS

Horisberger, "Colloidal Gold as a tool in molecular biology", TIBS, Nov., 1983 pp. 395–397.

Roth, "The Colloidal Gold Marker System for Light and Electron Microscopic Cytochemistry," in *Immunocytochemistry 2*, Academic Press, London, (1984), pp. 217–284.

*Primary Examiner*—Christopher L. Chin

[57] ABSTRACT

An aggregate for qualitatively or quantitatively determining bindable substances. Said aggregate comprises an ultra small colloidal particle and a specific binding agent characterized in that the mean diameter of the colloidal particle is below 2 nm. Preferably the size of the metal particle is selected so that the aggregate is capable of penetrating in standard biological specimens. The invention further provides a universally applicable detection system for determining bindable substances in particular in living material. Further there is provided a process for preparing said aggregate.

9 Claims, No Drawings

UNIVERSALLY APPLICABLE DETECTION SYSTEM BASED ON ULTRA SMALL COLLOIDAL METAL PARTICLES

This is a continuation of application Ser. No. 08/160,449, filed Dec. 1, 1993, now abandoned, which was a continuation of application Ser. No. 08/034,640, filed Mar. 22, 1993, now abandoned which was a continuation of application Ser. No. 07/920,028, filed Jul. 27, 1992, now abandoned which was a continuation of application Ser. No. 07/271,798, filed Nov. 15, 1988, now abandoned which is hereby incorporated by reference.

BACKGROUND OF THE INVENTION

During the last years, small size metal particles, in particular colloidal gold particles, have increasingly been used for the detection and/or quantitative determination of specific binding agents and/or their corresponding bindable substances. Usually, such bindable substances are of biological origin and their determination by means of metal labelling has proven useful in various areas of biochemistry, pharmacology, cytology and histology. The concerned techniques have found widespread use and are particularly attractive for diagnostic purposes.

In principle, the use of colloidal metal particles as markers is based on the fact that the specific binding agent or any substance bindable thereby, when brought into contact with the colloidal metal particles under appropriate conditions, do strongly absorb thereon without loosing their affinity for their binding or bindable counterpart. Mostly, the relationship between a specific binding agent and its corresponding bindable substance(s) will be of the type, antigen-antibody, antibody-antigen, protein-protein, protein-ligand, receptor-ligand or nucleic acid-complementary nucleic acid. Hence, the thus labelled specific binding agents or bindable substance, when allowed to interact with their counterparts will attach their label to the complex formed during the interaction and consequently the detection thereof can easily be performed making use of the properties of the colloidal metal particles.

Depending on the circumstances, colloidal metal particles can be detected, e.g., by direct visual examination, by microscopic or spectrofotometric techniques. A description of "the immunogold staining (IGS) technique", "the sol particle immuno assay (SPIA) technique" of specific applications and improvements thereof can be found in, e.g., U.S. Pat. Nos. 4,313,734, 4,446,238, 4,420,558, 4,775,636, and 4,752,567, and in IBRO handbook series, Wiley, N.Y., 1983, pages 347 to 372.

So far colloidal metal markers with a wide variation in particle sizes have been prepared. Typical examples are described in Techniques in Immunochemistry Vol. 2 (1983) and in the Journal of Histochemistry and Cytochemistry 35, 1191–1198 (1987) and the references described therein. Usually they are applied in a size range between 5 and 20 nm, however some small size colloidal metal markers of about 2.6 nm have been described in Histochemistry (1985) 83: 409–411. Detection systems based on small colloidal metal markers have a number of advantages over specific binding agents marked with larger metal particles. More particularly they give a higher labelling density and offer an increase in resolution for Electron Microscopy. However, detection systems based on these small colloidal metal particles have hardly been studied due to their instability and lack of reproducibility. It is therefore an object of the invention to provide reproducible detection systems based on stable and bio-compatible ultra small metal particles.

DESCRIPTION OF THE INVENTION

The present invention thus provides an aggregate for determining qualitatively or quantitatively bindable substances comprising a colloidal metal particle and a specific binding agent for said bindable substance characterized in that the mean diameter of the colloidal metal particles is ranging between 2 and 0.8 nm. In a further aspect the present invention provides an aggregate for determining bindable substances comprising a colloidal metal particle and a specific binding agent for said bindable substance characterized in that the size of the metal particle is selected so that said aggregate is capable of penetrating into standard biological specimens.

In still a further aspect of the invention there is provided a method for determining a bindable substance using the above identified aggregate.

The aggregate of the present invention is particularly suited for the determination of immunochemical components, such as, haptens, antigens and antibodies.

The colloidal particles of the present invention are either colloidal gold, silver, platinum, palladium, thalium, copper or nickel particles. Preferred examples of particles include gold, silver and platinum particles, with gold particles being the most preferred. Further, the particles may be radioactive, that is, radioactive gold particles, radioactive silver particles and radioactive platinum particles and the like.

In general the preparation of ultra small colloidal metal particles of the present invention is based on the homogeneous reduction of a suitable amount of an appropriate salt, acid or complex of the required metal with a strong reductant at low temperature so as to cause the salt, acid or complex to be reduced to form ultra small colloidal metal particles which are dispersed in a dispersion medium, such as water, straight chain or branched alcohols each having 1 to 10 carbon atoms, e.g. ethanol or methanol, water-miscible ethers e.g. dioxane or diethyl ether, and mixtures thereof. Preferred metal salts, acids or complexes include potassium tetrachloro-platinate, silver nitrate, chloroauric acid and the like salts, acids and complexes, or their radioactive isotopes. An effective reducing agent in the process is phosphorus, in particular white phosphorus, which is added in a stoichiometric amount or in a slight excess. Suitable conditions for this process include a pH value between about 2 and 11, a temperature between 0° and 10° C., preferably below 4° C. and vigorous stirring, varying between 100–1000 r.p.m. The reduction reaction may be instantaneous or may last as long as 10 minutes and is indicated by the appearance of a specific colour, such as, for example, brown in case of colloidal gold.

In a presently preferred embodiment the homogeneous reduction is effected at a temperature between 0°–4° C. by i) preparing an aqueous solution of an appropriate salt, acid or complex of the required metal; ii) preparing an aqueous suspension of phosphorus by mixing water with an appropriate amount of a saturated solution of phosphorus in a lower alkanol, e.g. ethanol or an ether, e.g. diethyl ether: iii) quickly adding one of the solutions to the other under vigorous stirring to form a colloidal sol; iv) and, if desired, removing the excess of reductant and/or the lower alkanol or ether from the sol at a low temperature, preferably at a temperature below 10° C., optionally under reduced pressure.

In particular, ultra small colloidal gold particles may be prepared by mixing during a limited period of time at a temperature between 0° and 4° C., one volume unit of 0.005–0.01% tetrachloroauric acid solution and one volume unit of an aqueous suspension of white phosphorus. The latter being prepared by addition of 0.0050–0.0075 volume units of a clear and saturated solution of white phosphorus (4° C.) in ethanol to approximately one volume unit of distilled water. Subsequently the excess amount of reductant is removed at a temperature below 10° C. under reduced pressure after addition of a sufficient amount of base to convert the remaining phosphorus to phosphine, if desired, the remaining traces of reductant can be removed by oxidation by passing air through the sol, or by addition of an oxidant, e.g. hydrogen peroxide.

Measurement of the colloids by use of a transmission type of electron microscope of model Philips EM 420 shows that the mean diameter of the ultra small colloidal metal particles in the thus prepared colloidal metal sol is ranging between 0.8 and 2 nm, in particular between 1 and 1.8 nm, preferably below 1.6 nm and that the size distribution is bell curved. The variation coefficient being less than 20%, usually less than 15%, in particular between 12% and 6%. It is contemplated that the thus prepared colloidal metal particles have a crystalline core and consist of at least three metal atoms. It is further assumed that the preferred colloidal metal particles contain between 12 and 600 metal atoms.

The attachment to specific agents or any agents bindable thereby and the various methods of combining them, directly or indirectly, with the desired bindable substances is similar to those methods known in the art. In this connection reference is made to U.S. Pat. Nos. 4,313,734 and 4,775,636 which are incorporated herein by reference; immunohistochemistry, Cuello, A. C. (ed.), IBRO handbook series, Wiley, N.Y., 1983, pages 347 to 372, Techniques in Immunocytochemistry Vol. 2, pages 217 to 284 (1983) and Immunochemistry, Wright, Bristol, 1986 pages 115 to 146.

For example, the attachment of the specific binding agent is easily effected by contacting the ultra small metal particles preferably at a temperature between 0° and 10° C. with an aqueous medium of appropriate pH wherein the desired binding agents, e.g., antibodies, are dissolved. An appropriate pH being between 4.5 and 10. In order to protect the particles from non-selective interactions with non-specific proteins of the test samples it may be appropriate to add quenching or stabilizing agents such as, for example, immunochemically inert polar macromolecules, e.g., bovine serum albumin (BSA), polyvinyl pyrrolidone (PVP) and polyethylene glycol (PEG). After a suitable period of time the aggregates can be concentrated and dialysed via art-known procedures e.g. vacuum dialysis.

The thus prepared aggregates are relatively stable and reproducible when compared with the unbound ultra small colloidal particles especially when the desired binding agents, e.g. antibodies and/or their fragments are attached to the colloids immediately after the preparation of the sol. This property can easily be demonstrated by measurements of the particle size with electron microscopy or by the absense of changes in the absorption spectrum in the visible spectrum ranging between 480 and 540 nm.

It was surprisingly found that the mean ratio between the colloidal metal particles and the binding agents in the thus prepared aggregates is at least one, and in particular about 2 which property was indicated by the statistical analysis of the single vs multiple particles frequency of aggregates in electron micrographs.

Another point which should be emphasized in comparison with the prior-art detection systems is the ability of the present aggregates to penetrate into standard biological specimens, in particular into cryosections and chemically fixed intact cells. Probes based on 3 nm particles and larger do not penetrate into standard biological specimens, unless after extensive treatment of the preparates with detergents, in which the biological structural coherence is strongly destroyed. An important factor which co-determines the penetrative capacities of an aggregate is the physical diameter of the aggregate formed by the metal particle and the binding agent. The hydrodynamic radius of the colloidal metal particle is about 50% larger than the actual physical diameter of the solid particle. It is known that the hydrodynamic radius is decreased after absorption of the specific binding agent, which implies that for aggregates with gold particles smaller than 5 nm the actual radius is largely determined by the radius of the binding agent itself. This in turn means that the penetrative capacity of a "3–5 nm aggregate" and a "1 nm aggregate" should not differ essentially.

In contrast herewith, there has now been found that immunoglobulin (IgG) coupled with one or more ultra small colloidal particle(s) does penetrate into cryosections whereas 4 nm gold particles coated with protein A do not.

The aggregates of the present invention do not only penetrate into cryosections but also penetrate into chemically fixed intact cells being optionally permeabilized in a very smooth way, for example, by treatment with 0.05–0.5% Triton X-100 during 1–15 minutes after fixation with 0.5–1% glutaraldehyde in PBS-buffer (10 mH phosphate buffer; 150 mH NaCl, pH 7.4) or with 0.1% saponin in PHEM-buffer (1 mM MgSO4; 10 mM EGTA; 60 mM PIPES; 25 mM HEPES; pH 6.9) during 1–15 minutes after fixation with 0.5–1% glutaraldehyde.

Under similar conditions, some aggregates of the present invention even penetrate into the nuclei of eukaryotic cells such as, PTK-2 cells.

Further it should be noted that in gel-filtration experiments, with for example Ultro gel ACA 44® (LKB), the specific binding agents being bound with one or more ultra small metal colloidal particle behave in a similar way as uncoupled specific binding agents, whereas aggregates based on larger colloidal metal particles behave as high-molecular weights.

As substances which can be detected according to the invention there may be mentioned any substance for which a specific binding agent exists. For example such substances comprise but are not limited to cell surface and tissue antigens, receptors, biological substances excreted by or derived from living organisms, particularly biological substances occurring in biological fluids such as saliva, lymph, blood and its derived fractions such as, plasma and serum, urine, cerebrospinal fluid, amnion fluid, and the like. Substances which can be detected include, proteins, polypeptides, peptides, like enzymes, hormones, structural proteins, receptors, nucleic acids, vitamins, polysaccharides, toxins, alkaloids, glycoproteins, haptens, metabolites, pharmacological agents, pesticides, pollutants, steroids, and any other molecule for which a specific binding counterpart exists in biological systems or can be synthesized.

The specific binding agents which can be used according to the invention can be of various nature but will in many instances be antibodies to specified antigens or haptens. As antibodies there may be mentioned, immunoglobulins such as, IgM, IgG, IgA, IgD, and IgE, IgG being preferred, and their fragments, e.g., Fc, Fab and F(ab)2. Antibodies may be polyclonal or monoclonal. As an example of specific binding substances other than antibodies there can be mentioned Staphylococcus Aurus protein A which specifically binds immunoglobulins of various animal species, protein G, steptavidin and avidin, other bindable substances may be phages, which are optionally chemically or genetically adapted to bind molecular or cellular materials, lectins, which specifically bind glycoproteins, DNA or RNA probes for gene identification, or fragments thereof and drugs which have a sufficient specificity and affinity for receptors. In general any other molecular interaction of sufficient specificity and affinity can be employed.

Representative protein analytes include the classes of protamines, mucoproteins, glycoproteins, globulins, albumins, scleroproteins, phosphoproteins, histones, lipoproteins, chromoproteins, and nucleoproteins. Examples of specific proteins are prealbumin, $\alpha_1$-lipoprotein, human serum albumin, $\alpha_1$-acid glycoprotein, $\alpha_1$-anti-trysin, $\alpha_1$-glycoprotein, transcortin, thyroxine binding globulin, haptoglobin, hemoglobin, myoglobin, ceruloplasmin, $\alpha_2$-lipoprotein, $\alpha_2$-macroglobulin, $\beta$-lipoprotein, erythropoietin, transferin, hemopexin, fibrinogen, the immunoglobulins such as IgG, IgE, IgM, IgA, IgD, and IgE, IgG being preferred and their fragments, e.g., Fc, Fab and F(ab)$^2$ complement factors, prolactin, blood clotting factors such as fibrinogen, thrombin and so forth, insulin, melanotropin, somatotropin, thyrotropin, follicle stimulating hormone, luteinizing hormone, gonadotropin, thyroid stimulating hormone, placental lactogen, intrinsic factor, transcobalamin, serum enzymes such as alkaline phosphatase, lactic dehydrogenase, amylase, lipase, phosphatases, cholinesterase, glutamic oxaloacetic transaminase, glutamic pyruvic transaminase, and uropepsin, endorphins, enkephalins, protamine, tissue antigens, bacterial antigens, and viral antigens such as hepatitis associated antigens (e.g., HBsAg, HBcAg and HBeAg).

Representative hapten analytes include the general classes of drugs, metabolites, hormones, pesticides, pollutants, vitamins, and the like organic compounds. Haptenic hormones include thyroxine and triiodothyronine. Vitamins include vitamins A, B, e.g. $B_{12}$, C, D, E and K, folic acid and thiamine. Drugs include antibiotics such as aminoglycosides, e.g., gentamicin, tobramycin, amidacin, sisomicin, kanamycin, and netilmicin, penicillin, tetracycline, terramycin, chloromycetin, and actinomycetin; nucleosides and nucleotides such as adenosine diphosphate (ADP) adenosine triphosphate (ATP), flavin mononucleotide (FMN), nicotinamide adenine dinucleotide (NAD) and its phosphate derivative (NADP), thymidine, guanosine and adenosine; prostaglandins; steroids such as the oestrogens, e.g., oestriol and oestradiol, steroids; and others such as phenobarbital, phenytoin, pirimidone, ethosuximide, carbamazepine, valproate, theophylline, caffeine, propranolol, procainamide, quinidine, amitryptiline, cortisol, desipramine, disopyramide, doxepin, doxorubicin, nortryptiline, methotrexate, imipramine, lidocaine, N-acetyl-procainamide, amphetamines, catecholamines, and antihistamines. Further cardiac glycosides, and derivatives of benzodiazepine, benzimidazole, piperidine, piperazine, imidazole, triazole, pyridazine, 1,2,4-triazinedione or 2,3,5, 6-tetrahydro-imidazo[2,1-b]thiazoles, or amides, hydratropic acid derivatives or trialkylamines.

Benzimidazole haptens comprise thiabendazole, fuberidazole, ciclobendazole, oxibendazole, parbendazole, cambendazole, mebendazole, fenbendazole, flubendazole, albendazole, oxfendazole, nocodazole and astemizole. Piperidine haptens comprise diphenoxylate, phenoperidine, haloperidol, haloperidol decanoate, bromperidol decanoate, bromperidol, moperone, trifluperidol, pipamperone, piritramide, fentanyl, benperidol, droperidol, benzitramide, benzetimide, domperidone, sufentanil, carfentanil, alfentanil, dexetimide, milenperone, difenoxin, fluspirilene, penfluridol, pimozide, lorcainide, loperamide, astemizole, ketanserine, levocabastine, cisapride, altanserin, ritanserin, 3-[2-[4-(4-fluorobenzoyl)-1-piperidinyl]-ethyl]-2,7-dimethyl-4H-pyrido-[1,2-a]-pyrimidin-4-one, 3-[2-[4-[bis (4-fluorophenyl)methylene]-1-piperidinyl]-ethyl]-2-methyl-4H-pyrido[1,2-a]pyrimidin-4-one and 3-[2-[4-[[3-(2-furanylmethyl)-3H-imidazo[4,5-b]pyridin-2-yl]amino]-1-piperdinyl]ethyl]-2-methyl-4H-pyridol[1,2-a]pyrimidin-4-one.

Piperazine haptens include azaperone, fluanisone, lidoflazine, flunarizine, mianserine, oxatomide, mioflazine, clocinizine and cinnarizine.

Examples of imidazole haptens are metronidazole, ornidazole, ipronidazole, tinidazole, isoconazole, nimorazole, miconazole, burimamide, metiamide, metomidate, enilconazole or imazalil, etomidate, econazole, clotrimazole, carnidazole, cimetidine, doconazole, sulconazole, parconazole, orconazole, butoconazole, triadiminole, tioconazole, valconazole, fluotrimazole, ketoconazole, oxiconazole, lombazole, bifonazole, oxmetidine, fenticonazole, tubulazole and (Z)-1-[2-chloro-2-(2,4-dichlorophenyl)-ethenyl]- 1H-imidazole. Triazole haptens comprise virazole, azaconazole, etaconazole, propiconazole, penconazole, itraconazole and terconazole. Pyridazine haptens comprise for example, 3-chloro-6-[3,6-dihydro-4-(3-methylphenyl)-1(2H)-pyridinyl]-pyridazine, 3-methoxy-6-[4-(3methyl-phenyl)-1-piperazinyl]pyridazine and the compounds of EP-A-156,433.

1,2,4-Triazinediones comprise for example, 2-chloro-$\alpha$-(4-chlorophenyl)-4-(4,5-dihydro-3,5dioxo-1,2,4-triazin-2 (3H)-yl)benzeneacetonitrile, 2,6-dichloro-$\alpha$-(4-chlorophenyl-4-(4,5dihydro-3,5-dioxo-1,2,4,-triazin-2(3H)-yl)benzeneacetonitrile and the compounds of EP-A-170, 316.

Trialkylamines are, for example, diisopromine, prozapine. 2,3,5,6-Tetrahydroimidazo[2,1-b]thiazoles comprise, for example, tetramisole or levamisole. Amides comprise for example, closantel, ambucetamide, isopropamide, uzepide metiodide, dextromoramide. A hydratropic acid hapten is, for example, suprofen.

The binding reaction will in almost all cases be allowed to proceed under mild conditions. The reaction mixture will in general be an aqueous medium with any desirable organic co-solvents being present in minor amounts. The temperature of the reaction will be maintained at a constant level in normal circumstances throughout the incubation period. Temperatures will generally be between 0° and 50° C., more usually between 20° and 40° C. Preferably the reaction will proceed at room temperature. The pH of the reaction mixture will vary between 5 and 10, more usually between 6 and 9. The concentration of various reagents will depend on the level of analyte expected in the test medium, with such level usually being between $10^{-3}$ and $10^{-12}$M. As in the case of the previously described reaction parameters, election is primarily based on empirically derived optimization balanced against the preferences and needs of the technician who will ultimately perform assays on a routine basis. None of the parameters therefore is of a critical nature to the present invention, rather they are all within the ordinary ranges used in the art.

The aggregates of the present invention can be employed in virtually all circumstances for which immunological techniques are conceived at present, especially those techniques which in general apply colloidal metal particles coupled to well defined organic substances. However, due to the penetrative capacities of the present aggregates the use will not be limited to those instances where at present metal labelling is known to be useful. In principle it can be applied to the qualitative and/or quantitative determination of any substance for which specific binding agents exist.

The aggregates of the present invention are particularly useful in those areas using specific detection techniques. For example in light or electron microscopic applications or blotting techniques, optionally in combination with chemical enhancement techniques e.g. silver enhancement, electronic enhancement techniques, electron energy loss detection techniques and/or X-ray micro analysis. Appropriate silver enhancement techniques are described in for example, the EP-A 165,634, in U.S. Ser. No. 23,733 and in Histochemistry 85, 209–214 (1986). Appropriate electronic enhancement techniques are for example described in U.S. Pat. No. 4,752,567. All incorporated herein by reference for their method of detection.

In light microscopical applications the present aggregates are especially useful for the immunological detection of antigens in combination with chemical enhancement, particularly silver enhancement, both in cell and tissue sections and in whole mount (intact cell) specimens. The thus achieved sensitivities are very high due to the fact that a large number of antigens are reachable for the penetrating aggregate and a higher labelling density is obtained as a result of the reduced steric hinderance. For example, the results for labelling tubulin are comparative or better than those which were achieved on basis of the same specific antibody labelled with an immunofluorescence marker. Besides, the signal generated is permanent and not prone to rapid degradation and no special microscopic equipment is needed. The resulting labelling after silver enhancement is particulate and can be quantified.

In electron microscopical applications the present aggregates are especially suited for high-resolution studies on distinct macromolecules or fragments thereof. The fact that the aggregates according to the present invention are capable of penetrating in standard biological specimens without any special pre-treatment makes them particularly useful in electron microscopical applications, e.g., to study the substructure of living material such as cells. In combination with chemical enhancement, they are suitable for immunolocalisation experiments, such as, preembedding immunolabelling of cells or tissue slices; post-sectioning labelling on plastic embedded material or cryosections; and labelling on whole mount cells. Preembedding labelling after mild permeabilization provides for efficient labelling with high sensitivity (penetration and efficiency), combined with optimized ultrastructural preservation. The resulting labelling after silver enhancement is particulate and can be quantified.

In blotting applications the present aggregates are especially suited for the identification of proteins in electrophoretically separated protein patterns. Compared to existing aggregates the detection is more sensitive and the resulting staining pattern is more delineated.

Due to their general character the aggregates of the invention, if desired, in combination with an enhancement technique the aggregates may further find utility in a variety of diagnostic tests such as, for example, the following: the detection and characterisation of subpopulations of T-lymphocytes; pregnancy tests based on the presence of certain hormones (chorionic gonadotropin) in the urine, diagnostic tests for various infections diseases of i.a. fungal, bacterial and in particular viral origin such as, for example, hepatitis B, auto-immune-diseases (e.g. AIDS), gonorrhoea, rubella, poliomyelitis, and the like, diagnostics for metabolic, endocrinological and various endogenous diseases, including diagnostics for the detection of congenital malfunctions of embryos based on the presence of specific proteins in the amnion fluid.

EXAMPLE 1

Preparation of colloidal gold dispersion containing ultra-small gold particles.

In a 1 liter beaker 200 ml distilled water was rapidly stirred at 300 r.p.m. and at a temperature of 4° C. 1.2 ml of a solution of ethanol, saturated at 4° C. with white phosphorus was added over 15 seconds below the surface of the water, followed immediately by the addition of 200 ml of 0.005–0.01% aqueous tetrachloroauric acid. Completion of the reduction was indicated by the appearance of a brown color. The excess of the reduction agent was subsequently removed by vigorously stirring the sol under reduced pressure with a water jet pump during 5 minutes after the sol was adjusted to pH 11.5 with sodium hydroxide at 4° C.

EXAMPLE 2

Preparation of colloidal gold-labelled anti-rabbit immunoglobulin (Ig) antibodies.

Affinity-purified goat-anti-rabbit Ig antibodies were dialysed against 5 mM $NaHCO_3$ pH 9.8 during 24 hours at 4° C. The acidity of the gold sol was brought to pH 9.0 with 0.2M $K_2CO_3$ solution. 100 ml of this gold sol was stirred in a beaker at room temperature. 5 mg of the dialyzed antibodies were added to obtain a final concentration of 50 µg/ml. 1 Minute later, 1 g bovine serum albumin (BSA) was added predissolved in 10 ml 1 mM sodium hydroxide. The thus obtained aggregate was dialyzed by vacuum dialysis against TBS-buffer (20 mM Tris; 150 mM sodium chloride, 20 mM $NaN_3$; pH 8.2).

EXAMPLE 3

Penetration experiment (intact cells)

PTK-2 cells were grown on coverslips. Isolated coverslips were washed with PBS-buffer (10 mM phosphate buffer; 150 mM sodium chloride; pH 7.4) and fixed and/or permeabilized according to either one of the following procedures:

Method A

The cells were fixed and permeabilized with 0.5% glutaraldehyde in PBS-buffer and 0.2% Triton X-100 during 10 minutes. The cells were further permeabilized during 15 minutes with 0.5% Triton X-100 in PBS-buffer.

Method B

The cells were fixed with 0.5% glutaraldehyde in PBS during 10 minutes and permeabilized during 15 minutes with 0.5% Triton X-100 in PBS-buffer.

Method C

The cells were washed with PHEM-buffer (1 mM $MgSO_4$.7 $H_2O$; 10 mM EGTA; 60 mM PIPES; 25 mM HEPES; pH 6.9) and then fixed with a 0.5% glutaraldehyde solution in PHEM-buffer during 10 minutes. After washing with a PHEM-buffer, the cells were permeabilized with a 0.1% saponin solution in PHEM-buffer during 15 minutes and then washed again with PHEM-buffer.

Method D

The cells were fixed with 0.5% glutaraldehyde in PBS-buffer.

After the fixation and permeabilization, the specimens were treated with 0.1M $NaBH_4$ in buffer (PBS or PHEM)

during 15 minutes. The whole was washed successively with PBS- or PHEM-buffer (3×5 minutes) and with a TBG-buffer (20 mM Tris; 150 mM sodium chloride; 20 mM $NaN_3$; 0.1% (w/v) BSA; 0.1% (w/v) CWF-gelatin (Sigma G 7765) and saponin 0.1% if method C is used; pH 8.2). The mixture was preincubated with 5% normal goat serum in TBG-buffer (+saponin) during 20 minutes and incubated overnight with rabbit-anti-tubulin 1 mg/ml in TBG (+saponin), supplemented with 1% normal goat serum. After washing three times, each 15 minutes, with TBG-buffer (+saponin), the cells were incubated during 4 hours with secondary goat-anti-rabbit (IgG) antibody/colloidal gold aggregates (the antibody concentration is ±1 mg/ml in TBG-buffer, 1% (w/v) normal goat serum). The whole was washed three times during 10 minutes with TBG buffer (+saponin) and then three times during 10 minutes with PBS-buffer. After washing, the cells were postfixed with 2% (w/v) glutaraldehyde in PBS-buffer during 10 minutes. The whole was washed successively with PBS-buffer (3×10 minutes) and then with distilled water (3×1 minute). The contrast of the reaction complex was increased by silver amplification with Intense II® (Janssen Life Science products) for 15 minutes. The coverslips are dehydrated and embedded in Pertex® (Histo-Lab).

Results

Goat-anti-rabbit (IgG) antibody/ultra small colloidal gold (±1 nm) aggregates penetrated into cell specimens prepared according to the procedures A, B, C and D whereas goat-anti-rabbit (IgG) antibody/ colloidal gold (±5 nm) aggregates only penetrate into specimens prepared according to procedure A.

EXAMPLE 4

Penetration of ultra small gold probes into semithin cryosections.

Strength of labeling compared to section thickness.

CHEMICALS AND REAGENTS

Goal anti-rabbit IgG polyclonal antibodies were conjugated to ultra small gold particles as previously described. Normal goat serum, GAR-G5 nm and Inten SEII were purchased from Janssen Biotech, Olen/Belgium. PIPES, HEPES, bovine serum albumine and coldwaterfish gelatin were obtained from Sigma, St. Louis Mo.

Glutaraldehyde from BDH, Poole/United Kingdom.

All other chemicals were purchased from Merck, Darmstadt/FRG and were of PA grade. All culture fluids were obtained from Gibco Paisley/United Kingdom

CELL CULTURES

Chinese hamster ovary cells (CHO cells) were cultured in Eagle's minimal essential medium supplemented with 10% fetal bovine serum.

SPECIMEN PREPARATION

After release from nocodazole treatment (ref. De Brabander et al., Microtubules and microtuble inhibitors 1980 page 225–268; Cell Motility 1981 page 469–483), mitotic CHO cells in metaphases and telophases were fixed in 0.5% glutaraldehyde in 60 mM PIPES, 25 mM HEPES; 10 mM EGTA, 1 mM magnesium sulfate (PHEM buffer), pH 6.9 for 10 minutes.

Cells were embedded in 10% liquified gelation at 37° C. Next the cells were pelleted by centrifugation at 325 g/or 3 minutes (Eppendorf centrifuge). After soldification at 4° C., the gelation was fixed with 0.5% glutaraldehyde in PHEM buffer for 10 minutes. For cryoprotection, cell pellets were infused with 0.6–1.5–2.3M sucrose in PBS.

After cryoprotection cell blocks were cut of 1–2 $mm^3$.

CRYO-SECTIONING

Serial semithin cyrosections (thickness 0.2 and 0.4 μm) were cut on a Keichert $FC_4D$ cryoultramicrotone. The sections were attached to coverslips and stored overnight in PBS at 4° C.

IMMUNOLABELING

Sections were treated with sodium borohydride (1 mg/ml) in PBS for 15 minutes to reduce residual aldehyde groups. Next the sections were rinsed 3×5 minutes in PBS and 2×5 minutes PBS supplemented with 0.8 BSA, 0.1% cold water fish gelatin, 2 mM azide, pH 7.4 (PBG-buffer). A specific staining was blocked by incubating by the sections in 5% normal goat serum in PBG buffer for 20 minutes. Next the sections were incubated with a rabbit polyclonal antibody against tubuli's (diluted to 1 μg/ml in PBG buffer supplemented with 1% normal goat serum) for 60 minutes. Detection was done either with a goat antirabbit polyclonal antibody conjugated to 5 nm gold or to the ultra small gold particles. The surpluss of gold probe was washed away with PBG-buffer 3×15 minutes.

After rinsing the section in PBS, they were fixed in 2% glutaraldehyde in PBS for 20 minutes. Silver enhancement was used for the light microscopical visualisation of the gold signal. Specificity and method controls for the immunocytochemical staining were as follows: omission of the anti-tubulin antibody and/or the gold conjugated goat anti-rabbit IgG antibody. The sections were rinsed in distilled water and dehydrated in a graded series of ethanol.

After mounting, the preparations could be evaluated.

RESULTS

Sections incubated with the 5 nm gold conjugate and the ultra small gold conjugate both showed a staining of the microtubules and the bulk of non polymensed tubulin in the cytoplasm of CHO cells.

Background staining was in both cases negligible. However, when the ultra small gold probe was used the specific signal in a 0.4 μm section was for more stronger than in a serial 0.2 μm section. This observation was in contrast with the one where the 5 nm gold conjugate was used. There the signal intensity remained the same.

EXAMPLE 5

Penetration of ultra small gold probes into semithin cryosections. Transverse sectioning of immunogold labeled semithin cryosections.

Semithin cyrosections (thickness 0.4 μm) of CHO cells embedded in gelatin, were attached to the bottom of plastic Petri dishes. They were labeled with a 5 nm gold probe or with the ultra small gold probe, as described in Example 4. The 5 nm gold labeled cryosections were further processed for electron microscopical evaluation without silver enhancement. Silver enhancement times for the sections labeled with the ultra small gold probe lasted up to 4 minutes.

PLASTIC EMBEDDING AND SECTIONING

After being immuno stained the semithin cryosections were dehydrated in a graded series of ethanol and embedded in Epon in the Petri-dishes. After polymerization at 50° C. for 24 hours, the plastic dishes were removed and the sections were reembedded in flat molds in Epon for transverse sectioning.

Ultrathin plastic sections were cut on a Reichert ultracut E and picked up on grids with a carbon coated parlodion film. They were stained with uranyl acetate and lead citrate before examination in a Philips EM 410 electron microscope.

RESULTS

When treated properly, reembedded semithin cryosections showed a well preserved morphology although cracks and clefts could be seen.

Plastic cross sections through labeled and reembedded semithin cryosections allowed determination of the gold or goldsilver particles on or within the sections. After silver enhancement, the ultra small gold particles could be made clearly visible. A silver enhancement time of 2 minutes showed goldsilver particles approximating 5 nm.

Transverse sectioning showed that immunolabeling with 5 nm gold probes was confined to the surface of semithin cryosections if there was no visible damage. If there were cracks or clefts in the section, only on those sites the 5 nm particles could be seen inside the section. Semithin cryosections with a severely disrupted ultrastructure showed overall penetration of the 5 nm goldprobe.

Well preserved cryosections showed labeling with the ultra small goldprobe not only on the surface of the section, but also throughout the whole inside. Even cells with an intact outer cell membrane showed an intense labeling. Damaged semithin cryosections were also labeled throughout.

We claim:

1. A process for preparing an aggregate for determining substances comprising a colloidal metal particle and a specific binding agent for said substance whereby the mean diameter of said colloidal particle is ranging between 0.8 and 1.6 nm, whereby the colloidal metal particle is obtained by a homogeneous reduction of an appropriate salt, acid or complex of the required metal with the reductant phosphorus at a temperature ranging between 0 and 10 C.

2. The process according to claim 1 wherein the colloidal metal particles are either gold, silver, platinum, palladium, thalium, copper or nickel particles or the radioactive isotopes of said metals.

3. The process according to claim 1 wherein the mean ratio of the amount of colloidal metal particle to the amount of binding agent is at least 1.

4. The process according to claim 1 wherein the specific binding agent is an antibody, avidin, streptavidin, protein A or protein G.

5. The process according to claim 4 wherein the antibody is an immunoglobulin or a fragment thereof.

6. The process according to claim 1 whereby the homogeneous reduction comprises the steps of:
   i) preparing an aqueous solution of an appropriate salt, acid or complex of the required metal;
   ii) preparing an aqueous suspension of phosphorus by mixing water with an appropriate amount of a saturated solution of phosphorus in a lower alkanol or an ether;
   iii) quickly adding one of the solutions to the other under vigorous stirring to form a colloidal sol; and, if desired,
   iv) removing the excess amount of phosphorus and/or the lower alkanol or ether from the sol at a temperature ranging between 0° and 10° C.

7. A method of qualitatively or quantitatively detecting a substance, comprising
   (a) contacting the substance with the aggregate formed by the process of claim 1, which specifically binds the substance;
   (b) incubating the substance and the aggregate so contacted such that the aggregate specifically binds to the substance;
   (c) separating aggregate which is not specifically bound to the substance; and
   (d) detecting specifically bound aggregate thereby detecting the substance.

8. A process for preparing colloidal metal particles having a mean diameter in the range between 0.8 nm and 1.6 nm which comprises a homogenous reduction of an appropriate salt, acid, or complex of a required metal with a strong reductant at a temperature ranging between 0° and 10° C.

9. A process according to claim 8, wherein the homogenous reduction comprises the steps of
   i) preparing an aqueous solution of an appropriate salt, acid or complex of the required metal;
   ii) preparing an aqueous suspension of phosphorous by mixing water with an appropriate amount of a saturated solution of phosphorous in a lower alkanol or an ether;
   iii) adding one of the solutions to the other under vigorous stirring to form a colloidal sol; and,
   iv) removing the excess amount of phosphorous and/or the lower alkanol or ether from the sol at a temperature ranging between 0° and 10° C.

* * * * *